US007783582B2

(12) United States Patent
Doctor et al.

(10) Patent No.: US 7,783,582 B2
(45) Date of Patent: Aug. 24, 2010

(54) BAYESIAN-NETWORK-BASED METHOD AND SYSTEM FOR DETECTION OF CLINICAL-LABORATORY ERRORS USING SYNTHETIC ERRORS

(75) Inventors: Jason N. Doctor, Calabasas, CA (US); Gregory B. Strylewicz, Rockville, MD (US)

(73) Assignee: University of Washington, Seattle, WA (US)

( * ) Notice: Subject to any disclaimer, the term of this patent is extended or adjusted under 35 U.S.C. 154(b) by 631 days.

(21) Appl. No.: 11/827,449

(22) Filed: Jul. 10, 2007

(65) Prior Publication Data

US 2008/0222058 A1    Sep. 11, 2008

Related U.S. Application Data

(60) Provisional application No. 60/819,984, filed on Jul. 10, 2006.

(51) Int. Cl.
*G06F 17/20* (2006.01)
(52) U.S. Cl. .................................................. 706/12
(58) Field of Classification Search ............ 706/12, 706/14, 20, 45, 62
See application file for complete search history.

(56) References Cited

U.S. PATENT DOCUMENTS 6,687,685 B1 * 2/2004 Sadeghi et al. .............. 706/15

2003/0065535 A1 * 4/2003 Karlov et al. ................. 705/2

OTHER PUBLICATIONS

Sjobergh et al. Faking Errors to Avoid Making Errors: Machine Learning for Error Detection in Writing, 2005, Proceedings of RANLP, pp. 1-6.*
Onisko et al., A Bayesian Network Model for Diagnosis of Liver Disorders, 1999, Center for Biomedical INformatics, University of Pittsburgh, pp. 1-6.*
Zhu et al. Error Detection and Impact-Sensitive Instance Ranking in Noisy Datasets, 2004, American Association for Artificial Intelligence, pp. 378-383.*
Doshi et al., Using Bayesian Networks for Cleansing Trauma Data, 2003, American Association for Artificial Intelligence, pp. 1-5.*
Lin et al., Exploiting missing clinical data in Bayesian network modeling for predicting medical problems, 2007, Elsevier 1532-0464, pp. 1-14.*

* cited by examiner

*Primary Examiner*—David R Vincent
(74) *Attorney, Agent, or Firm*—Olympic Patent Works PLLC

(57) ABSTRACT

Embodiments of the present invention include methods and systems for analyzing clinical-laboratory results and data in order to detect erroneous clinical-laboratory results. Embodiments of the present invention employ Bayesian networks and modified Bayesian networks that are constructed using cleaned clinical-laboratory results into which various types of synthetic errors have been introduced and that are optimized using different, cleaned clinical-laboratory results into which synthetic errors have been introduced.

1 Claim, 19 Drawing Sheets

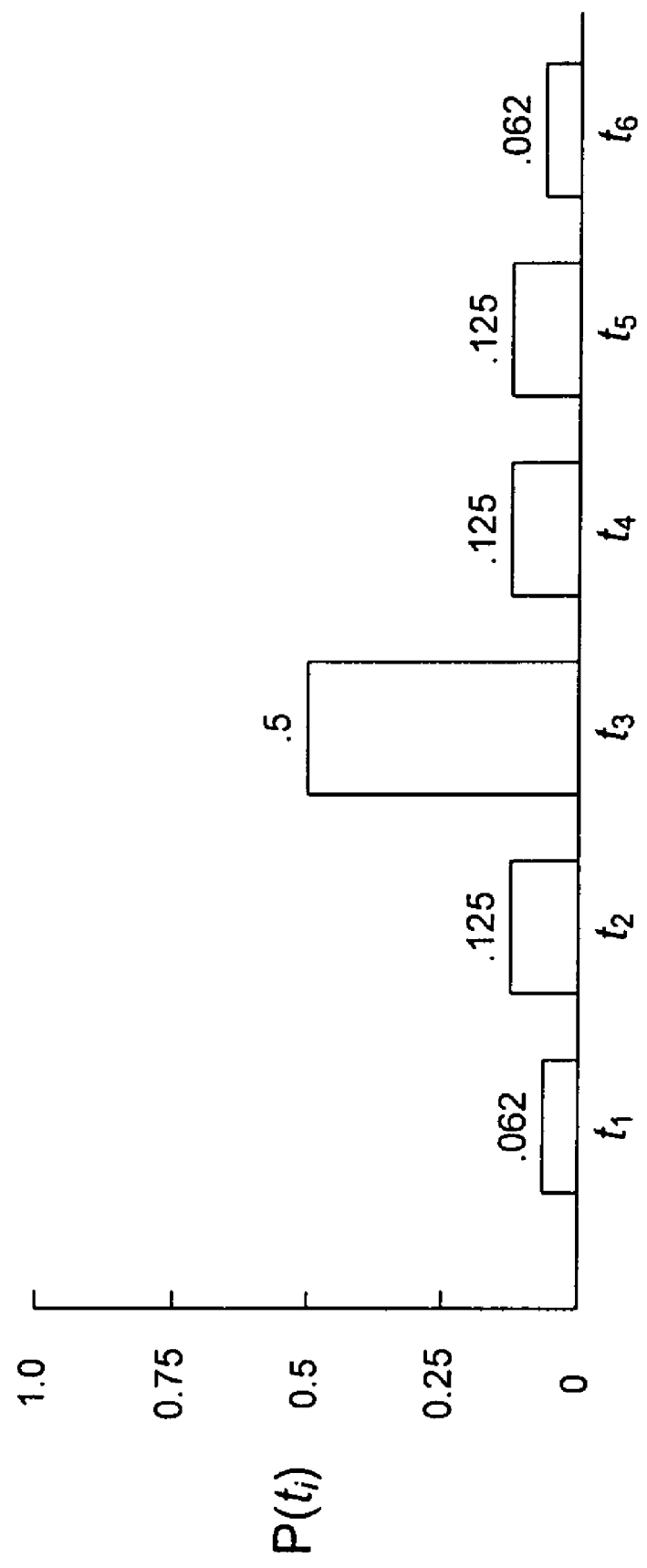

| patient | date | time | test A | test B | test C | test D | test E | test F | test G |
|---|---|---|---|---|---|---|---|---|---|
| 123801 | 7/21/06 | 13:21 | + | 0.61 | 5 | | | 167.3 | |
| 129762 | 7/21/06 | 13:46 | - | 1.32 | | | | 180.2 | |
| . . | . . | . . | | . . | | | | . . | |

806 points to 0.61 (value error)

Figure 8B

| patient | date | time | test A | test B | test C | test D | test E | test F | test G |
|---------|---------|-------|--------|--------|--------|--------|--------|--------|--------|
| 123801 | 7/21/06 | 13:21 | -      | 1.66   | 5      |        |        | 167.3  |        |
| 129762 | 7/21/06 | 13:46 | -      | 1.32   |        |        |        | 180.2  |        |
| ...    | ...     | ...   | ...    | ...    | ...    | ...    | ...    | ...    |        |

808 → (circling test A "-" and test B "1.66" in first row)

sample processing error

Figure 8C

| patient | date | time | test A | test B | test C | test D | test E | test F | test G |
|---|---|---|---|---|---|---|---|---|---|
| 123801 | 7/21/06 | 13:21 | - | 1.32 | 5 | | | 167.3 | |
| 129762 | 7/21/06 | 13:46 | + | 0.16 | | | | 180.2 | |
| | | | | | | | | | |
| | | | | | | | | | |
| | | | | | | | | | |
| | | | | | | | | | |
| | | | | | | | | | |
| | | | | | | | | | |
| | | | | | | | | | |
| | | | | | | | | | |
| | | | | | | | | | |

810 sample switch

Figure 8D

| patient | date | time | test A | test B | test C | test D | test E | test F | test G |
|---|---|---|---|---|---|---|---|---|---|
| 123801 | 7/1/06 | 13:30 | - | 1.87 | | | | | |
| 123801 | 7/2/06 | 13:30 | - | 1.67 | | | | | |
| 123801 | 7/3/06 | 13:30 | - | 1.75 | | | | | |
| 123801 | 7/4/06 | 13:30 | - | 1.77 | | | | | |
| 123801 | 7/5/06 | 13:30 | + | 0.10 | | | | | |
| 123801 | 7/6/06 | 13:30 | - | 1.63 | | | | | |
| 123801 | 7/7/06 | 13:30 | - | 1.80 | | | | | |

812 (pointing to "+" and "0.10" in the 7/5/06 row)

Figure 8E

BAYESIAN-NETWORK-BASED METHOD AND SYSTEM FOR DETECTION OF CLINICAL-LABORATORY ERRORS USING SYNTHETIC ERRORS

CROSS-REFERENCE TO RELATED APPLICATION

This application claims the benefit of Provisional Application No. 60/819,984, filed Jul. 10, 2006.

TECHNICAL FIELD

The present invention is related to clinical laboratory analysis and, in particular, to a method and system for automated analysis of clinical-laboratory-analysis results to detect various types of errors.

BACKGROUND OF THE INVENTION

Clinical laboratory analysis of biological samples is a large and important commercial activity world wide, and is fundamental for medical-services provision, public health, environmental monitoring, occupational-health-and-safety monitoring programs, provision of veterinary services, and a wide variety of important services and programs provided both by private and commercial institutions, including medical clinics and hospitals, as well as public and governmental institutions. Often, results of clinical laboratory analysis provide the data upon which important medical, public health, and governmental-policy decisions are made. Errors in clinical-laboratory results may lead to incorrect diagnosis of health, environmental, occupational-safety, and other problems, leading at least to a need for repeating expensive clinical-laboratory tests and other such inefficiencies, and potentially leading to incorrect treatments, incorrect remedial measures, and injury or harm to people, domesticated animals, and the environment. For example, of the estimated seven billion medical laboratory tests conducted in the United States each year, approximately 70 million laboratory tests are estimated to produce erroneous results. These erroneous results are thought to result in tens of billions of dollars of unnecessary economic costs each year.

Clinical laboratories well understand the problem of erroneous clinical laboratory results, and currently apply a number of different methods to control and standardize laboratory procedures to prevent errors and to analyze clinical-laboratory results for any inadvertent errors that arise despite control and standardization. One method for analyzing clinical-laboratory results is to manually analyze results and data by laboratory and medical experts. Manual analysis of laboratory results relies on analysis of trends, over time, in the results generated for particular patients and on detecting various internal inconsistencies within laboratory-results data sets. Various automated clinical-laboratory-result analysis systems and methods have been developed, most employing rule-based expert systems and pattern-detection systems.

Both manual analysis and current automated analysis systems have significant drawbacks and deficiencies. For example, manual analysis that depends on observing trends in the results generated for particular patients is highly dependent on the frequency at which results are generated for the particular patients, the inherent variability of the different types of test results, and the patients' overall conditions. As a patient's condition departs further and further from a normal, healthy state, the variability of various clinical-laboratory results generated from samples taken from the patient may often markedly increase, leading to increased unpredictability of errors in the clinical-laboratory results. Laboratory experts are generally efficient error detectors, but, as with any human activity, the accuracy of manual clinical-laboratory-result analysis may suffer from fatigued or distracted analysts and from clerical errors. As another example, when a particular type of clinical-laboratory result has relatively large, intrinsic variability, it may be difficult to spot small, systematic variations indicative of erroneous results.

While internal consistency of clinical-laboratory results is an important target for manual and automated analysis, the many and often dynamical functional dependencies between different types of clinical tests and different types of clinical-test results may be difficult to discover, difficult to apply to large data sets, and extremely difficult to capture in simple logical rules on which expert systems are based. Rule-based expert systems are often proprietary and therefore opaque to users and regulators. Rule-based expert systems are notoriously brittle with respect to addition of new rules and modification of existing rules. Small changes to the rule base may often lead to unpredictable and unintended perturbations, similar to observed instabilities in chaotic systems with respect to initial conditions. Moreover, a rule-based expert system designed to detect clinical-laboratory errors cannot generally infer likely causes for the errors.

For all of these reasons, manual analysis and currently available automated analysis systems are generally incapable of ferreting out all of the potential errors that arise in reported clinical-laboratory-analysis results. Clinical-laboratory personnel, users of clinical-laboratory results, including medical professionals, public health professionals, veterinarians, and other users, and ultimately all who undergo medical treatment, pay for medical treatments, and live and work in environments monitored for health and safety, have therefore recognized the need for continued development of more effective and efficient clinical-laboratory-result error-detection methods and systems and the need to remain ever vigilant in evaluating and using clinical-laboratory results.

SUMMARY OF THE INVENTION

Embodiments of the present invention include methods and systems for analyzing clinical-laboratory results and data in order to detect erroneous clinical-laboratory results. Embodiments of the present invention employ Bayesian networks and modified Bayesian networks that are constructed using cleaned clinical-laboratory results into which various types of synthetic errors have been introduced and that are optimized using different, cleaned clinical-laboratory results into which synthetic errors have been introduced.

BRIEF DESCRIPTION OF THE DRAWINGS

FIG. 6A shows a simple discrete probability distribution of a random variable T, in which T can take on one of six discrete values $t_1$, $t_2$, $t_3$, $t_4$, $t_5$, and $t_6$ with the probabilities indicated both numerically and by height of the histogram columns in FIG. 6A.

FIGS. 8A-F illustrate a portion of an exemplary clinical-laboratory-analysis-result data set and various types of errors that may arise in clinical-laboratory-analysis-result data sets.

DETAILED DESCRIPTION OF THE INVENTION

Method and system embodiments of the present invention are directed to analysis of clinical-laboratory results in order to detect various types of clinical-laboratory-result errors. Various embodiments of the present invention employ Bayesian networks or modified Bayesian networks and receiver operating characteristic curves, described in initial subsections, provided below. In a final subsection, a number of embodiments of the present invention are described. Portions of a grant proposal for work related to the present invention are included in Appendix A. These portions of the grant proposal provide preliminary results obtained from initial implementations of embodiments of the present invention.

Receiver Operating Characteristic Curves

Receiver operating characteristic curves ("ROCC") were initially developed for applications in analysis of noise-contaminated radio signals and radar signals. More recently, ROCCs have proved to be useful in various types of clinical and medical-research analyses and decision-making processes.

Figure 1:
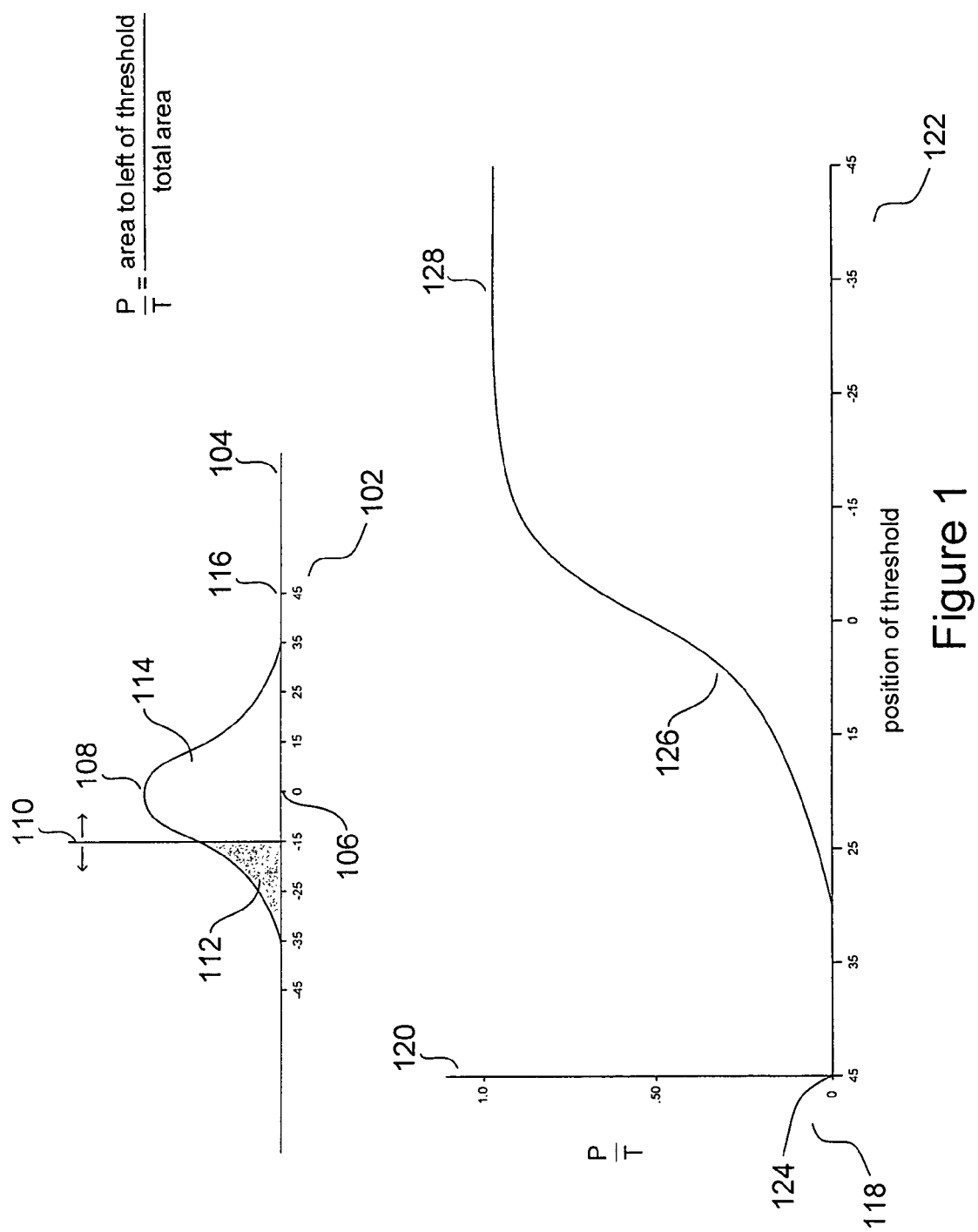
FIG. 1 illustrates threshold effects in sampling a population.

FIG. 1 illustrates threshold effects in sampling a population. In the top portion of FIG. 1, a Gaussian distribution 102 of a measured or sampled feature of individuals within the population is plotted. The Gaussian distribution may be produced, for example, by measuring a feature or characteristic of each individual in a population and plotting the number of individuals with each measured value. For example, features such as height and weight generally produce Gaussian, or normal, distributions when measured for each individual in a relatively large population of individuals. The measurements are usually plotted along the horizontal axis 104 in units of standard deviations, with the mean value of the measurements 106 having a corresponding to the peak 108 of the plotted distribution.

Consider a slightly different case in which a test is developed to determine whether or not each individual in a large population has a particular feature or characteristic. For example, the test may be used to determine which individuals in a population have antibodies to a particular virus in order to determine which individuals are virus-exposed. In this example, the test can produce continuous, numerical results over a range of numerical results, and the plotted Gaussian distribution 102 in FIG. 1 can be considered to represent the distribution of test-result values observed for individuals who have been exposed to the virus. In other words, the plotted distribution 102 represents antibody test results observed in a virus-exposed subpopulation selected from a larger population. Next consider setting a threshold value to a particular test-result value, with all individuals having test results results below the threshold value considered to not have been exposed to the virus, and all individuals with test results equal to, or greater than, the threshold value considered to have been exposed to the virus. In the plotted Gaussian distribution 102 in FIG. 1, one particular threshold is indicated by the vertical line 110. This particular setting of the threshold, represented by vertical line 110, results in those individuals of the virus-exposed subpopulation with test results below $-1\sigma$, represented by the shaded area 112, being deemed to be unexposed to the virus, while the remaining individuals of the virus-exposed subpopulation, represented by the unshaded area 114 below the Gaussian distribution curve, correctly deemed to have been exposed to the virus.

Next consider setting the threshold value to $4\sigma$ 116 and moving the threshold value lower along the horizontal axis 104 step-by-step, at each step determining the fraction of the virus-exposed subpopulation correctly identified as being virus exposed by the test and current threshold setting. The sensitivity curve 118 in FIG. 1 shows a plot of the percentage of virus-exposed individuals correctly deemed to be virus-exposed, plotted along the vertical axis 120, with respect to the threshold setting, plotted along the horizontal axis 122. As can be seen in FIG. 1, when the threshold is set at $4\sigma$ 116, no virus-exposed individuals are considered to be virus exposed by application of the test, as represented by the origin 124 in the sensitivity plot. As the threshold is moved to lower and lower values, the percentage of virus-exposed individuals correctly deemed as having been exposed to the virus rapidly rises 126 between threshold settings of $1\sigma$ and $-1\sigma$, and then falls off as the percentage of correctly identified virus-exposed individuals reaches 100 percent 128.

Figure 2:
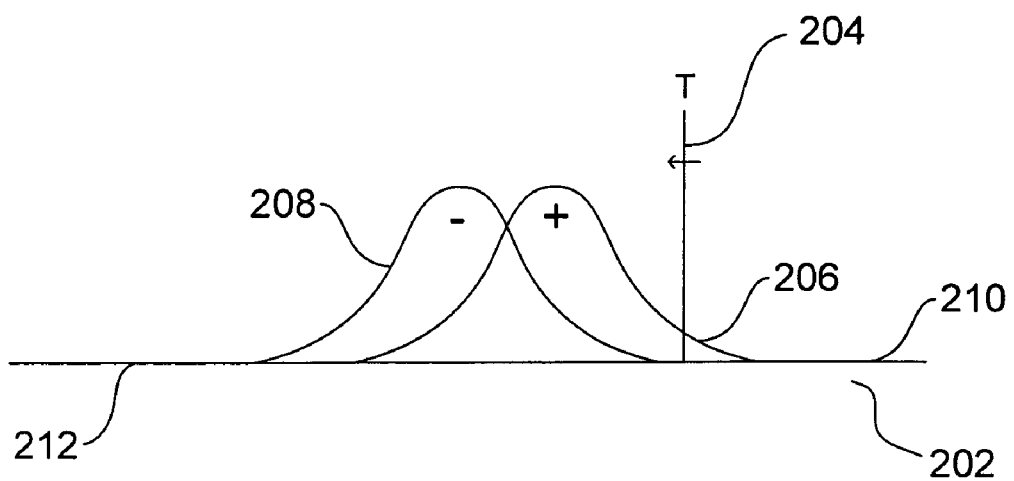
FIG. 2 shows a receiver operating characteristic curve and two subpopulations from which the receiver operating characteristic curve is generated.
Figure 2:
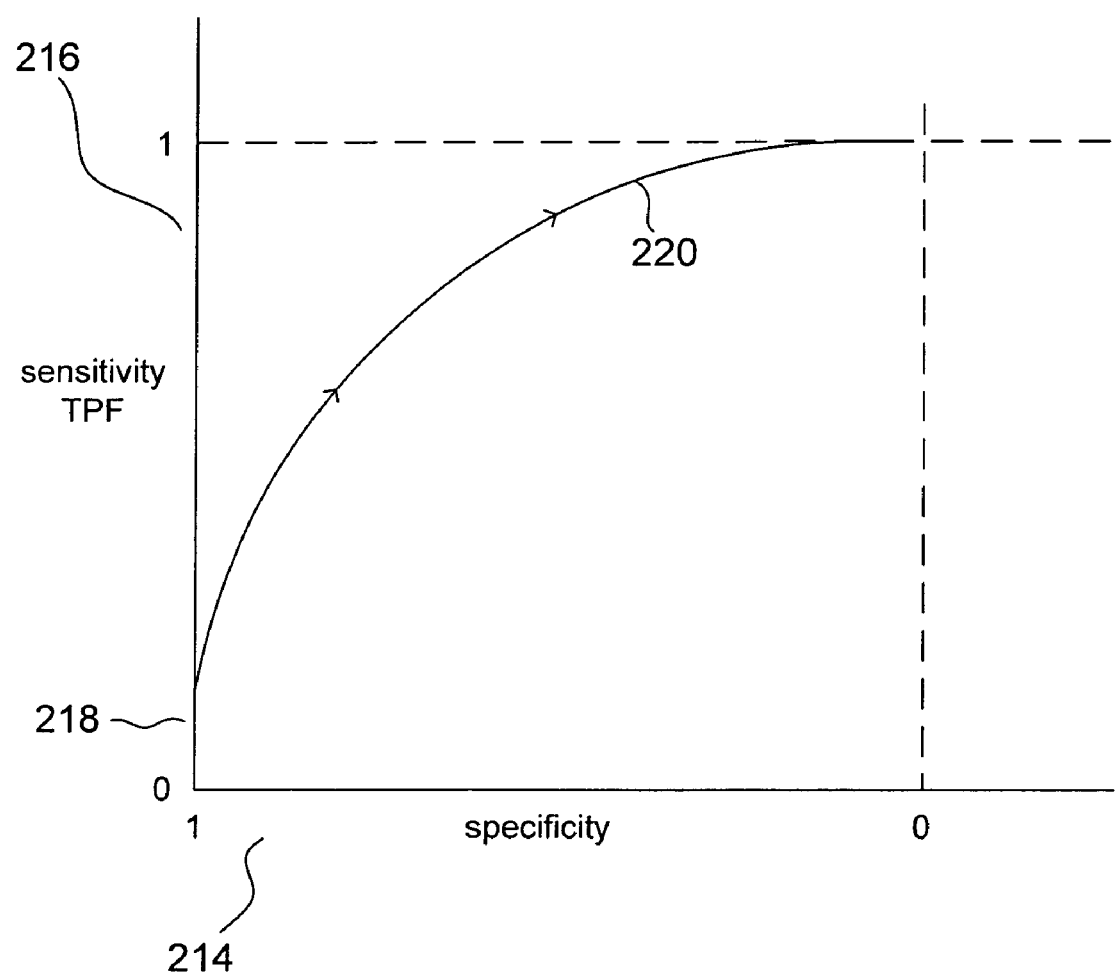

FIG. 2 shows a receiver operating characteristic curve and two subpopulations from which the receiver operating characteristic curve is generated. In FIG. 2, two Gaussian distributions are plotted 202. As in FIG. 1, a threshold 204 is shown at a particular setting with respect to the two Gaussian-distributed subpopulations. The first Gaussian subpopulation 206 represents those individuals exposed to the virus, and the second Gaussian population 208 represents those individuals not exposed to the virus. Again, as in the example discussed with reference to FIG. 1, a test is applied to each individual in the total population, represented by the sum of the areas below the two Gaussian distribution curves 206 and 208. As in FIG. 1, the threshold is moved from an initial high value 210 to a low value 212, and, at each threshold setting, the percentage of virus-exposed individuals correctly identified by the test, and the percentage of virus-unexposed individuals, incorrectly identified by the test, are determined and plotted in the ROCC 214 shown in the lower portion of FIG. 2. The fraction of virus-exposed individuals correctly identified by the application of the test with a particular threshold setting is referred to as the sensitivity of the test with the particular threshold setting, and is plotted along the vertical axis 216 in the ROCC. The percentage of individuals who have not been exposed to the virus that are not incorrectly identified as having been exposed to the virus by the test is referred to as the specificity of the test with the particular threshold setting. At first, when threshold settings are high, such as threshold setting 204, only virus-exposed individuals are detected by the test, and therefore the sensitivity increases vertically 218, since the specificity of the test is 100 percent.

However, as the threshold is lowered, more and more non-virus-exposed individuals are incorrectly identified having been exposed to the virus, leading to decrease in the specificity of the test. When the peaks of the Gaussian distributions for the two subpopulations are displaced, as shown in the population-distribution plots 202, the ROCC curve 220 shown in the ROCC plot 214 is generated. The ROCC plot illustrates the tradeoffs involved in setting a particular threshold. In general, one desires a test that provides both a high sensitivity and a high specificity. However, as the threshold is lowered to increase sensitivity, the specificity is inexorably lowered. Because of overlap of the subpopulations, there is no way to achieve 100 percent sensitivity without incurring a relatively low specificity.

Figure 3:
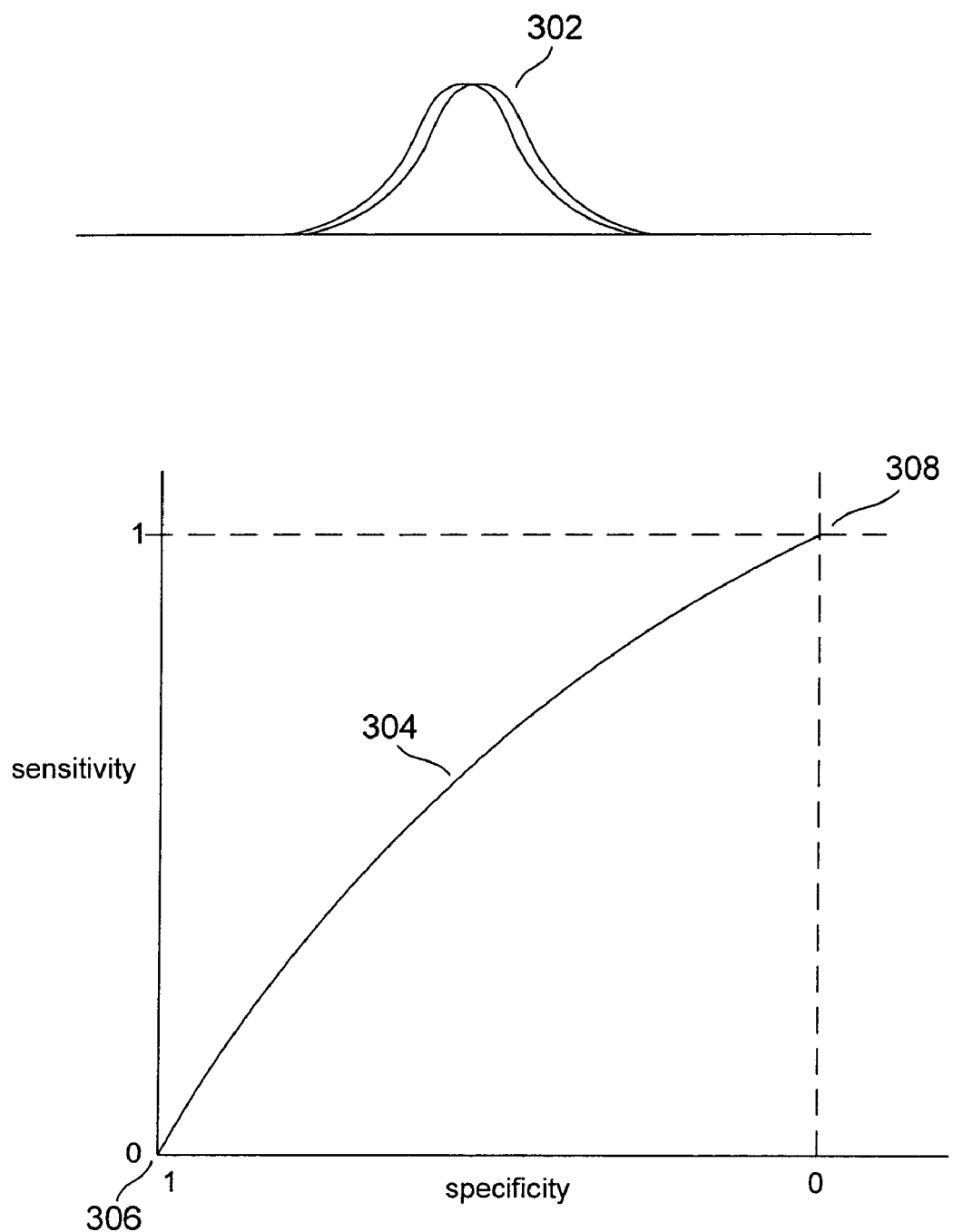
FIG. 3 illustrates an ROCC generated from two closely aligned subpopulations.
Figure 4:
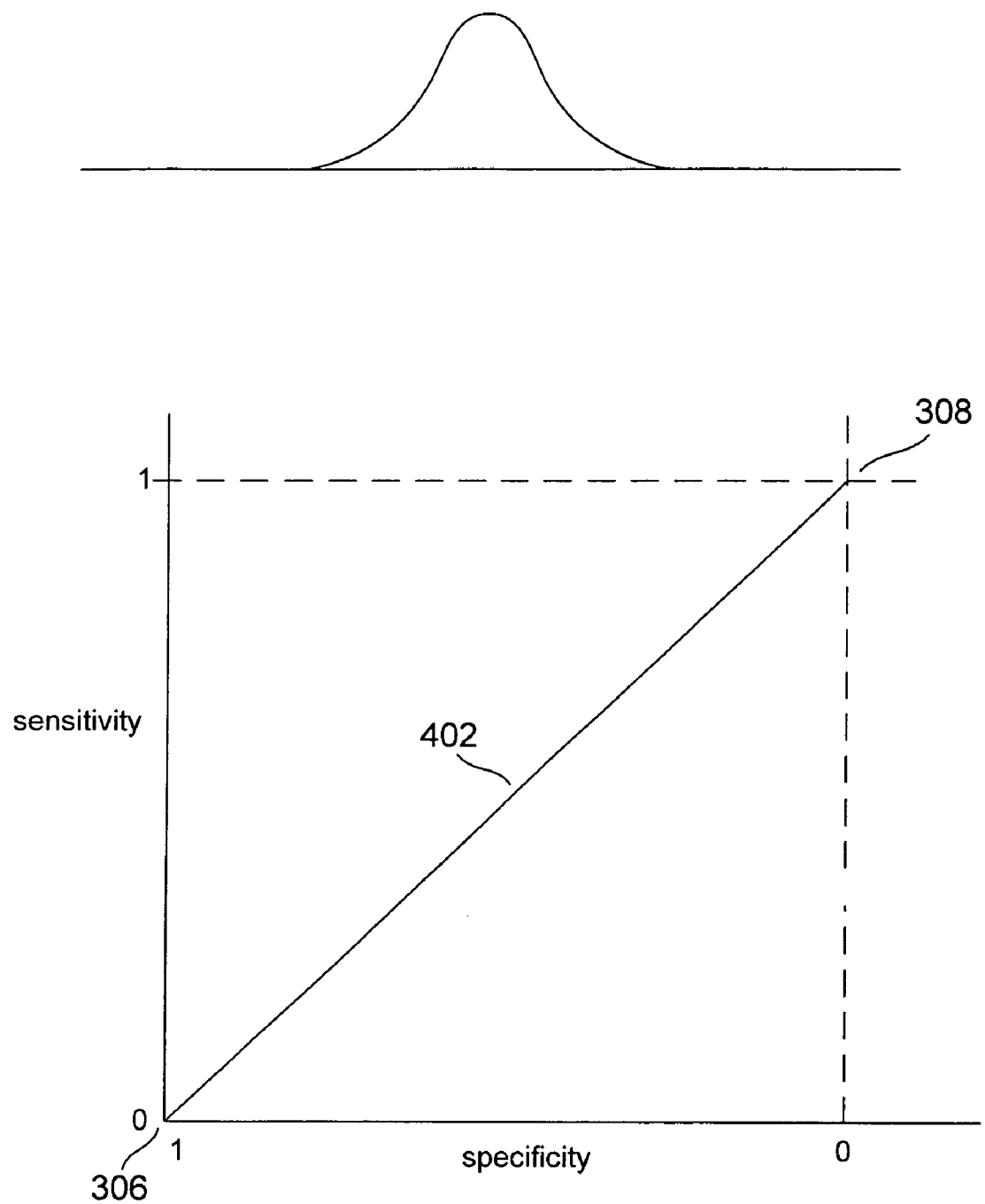
FIG. 4 shows an ROCC generated from two exactly aligned subpopulations.
Figure 5:
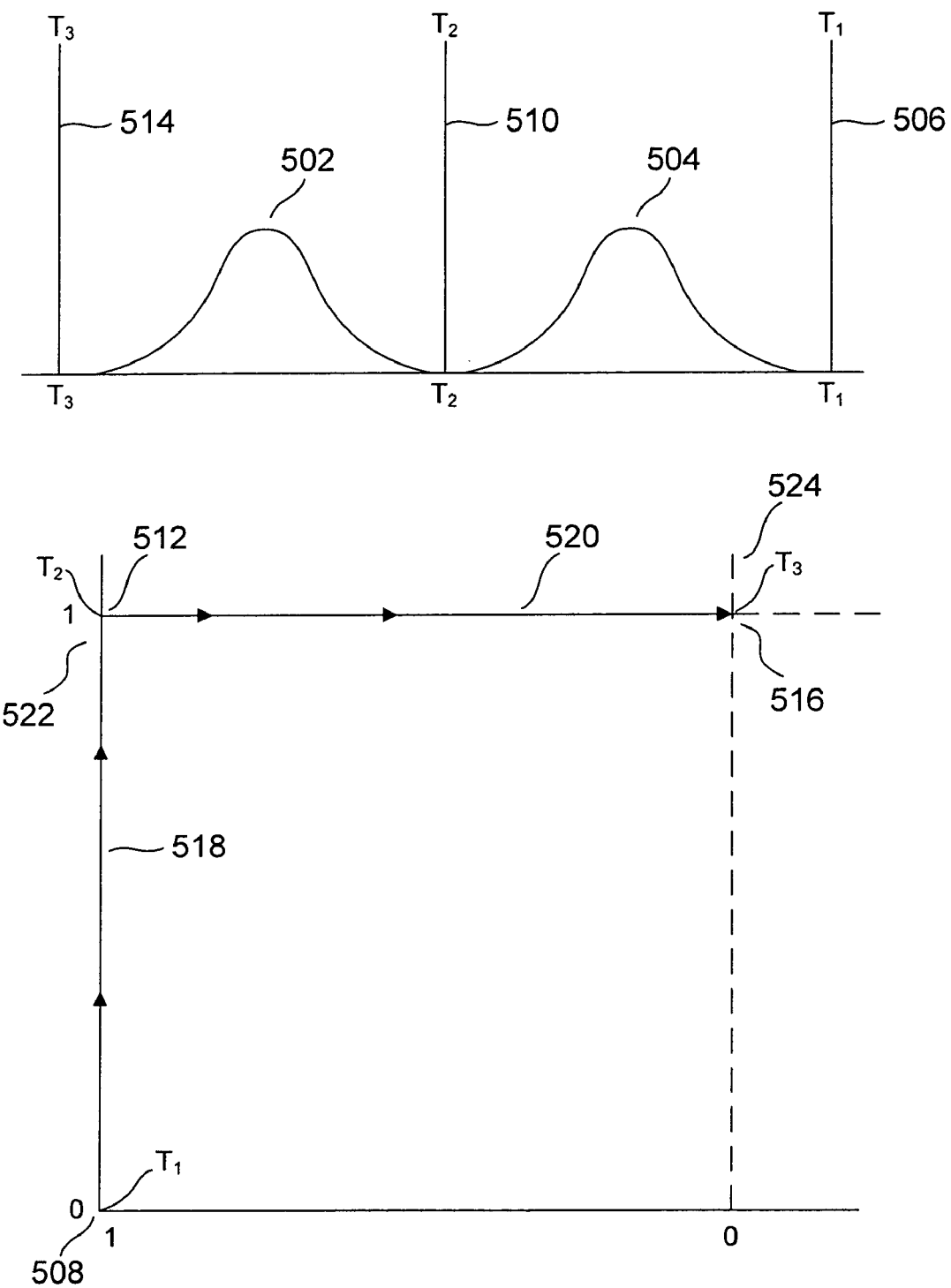
FIG. 5 shows an ROCC curve generated from two, non-overlapping, ideal subpopulations.

FIG. 3 illustrates an ROCC generated from two closely aligned subpopulations. FIG. 3, and FIGS. 4 and 5 which follow, use the same illustration conventions as used in FIG. 2. As the two Gaussian-distributed subpopulations more closely coincide 302, the ROCC curve 304 more closely conforms to a diagonal line connecting the origin 306 with the upper right-hand corner 308 of the plot. FIG. 4 shows an ROCC generated from two exactly aligned subpopulations. As seen in FIG. 4, the ROCC is a straight diagonal line 402 connecting the origin 306 with the upper right-hand corner 308 of the ROCC plot. The ROCC curve shown in FIG. 4 indicates that the test has no ability to discriminate individuals of one subpopulation from individuals of the other subpopulation. FIG. 5 shows an ROCC curve generated from two, non-overlapping, ideal subpopulations. As shown in FIG. 5, the first subpopulation 502 does not overlap the second subpopulation 504. When a threshold is set at $t_1$ 506, the test has zero sensitivity and 100 percent specificity 508. When the threshold is set at the value $t_2$ 510, the test has 100 percent sensitivity and 100 percent specificity 512. When the threshold is set at $t_3$ 514, the test has 100 percent sensitivity and zero percent specificity 516. Thus, in the ideal case, the ROCC is a straight vertical line rising from the origin 518 and a horizontal line 520 stretching from the left-hand upper corner 522 of the ROCC plot to the right upper-hand corner of the ROCC plot 524.

There are a number of different metrics that can be derived from an ROCC curve to indicate the desirability of a particular test combined with a particular test threshold for differentiating two subpopulations based on whether measured test values fall below, or are equal to, or greater than, a particular threshold. One metric is the area underneath the ROCC curve. In the ideal case, shown in FIG. 5, in which a threshold can be set to precisely and unambiguously differentiate the two subpopulations, the area under the ROCC curve is one. In the worst case, shown in FIG. 4, the area underneath the ROCC curve is ½. Were the ROCC curve to fall below the diagonal ROCC curve shown in FIG. 4, then the meaning of the test could be inverted to produce an ROCC curve with an area below the ROCC curve greater than 0.5. Thus, an ROCC curve with an area under the ROCC curve of 0.5 represents the worst case.

ROCC curves can be effectively employed with un-normalized data and with data distributed according to any number of different probability-distribution models. In various embodiments of the present invention, ROCC curves can be generated for results of analyzing clinical-laboratory data into which synthetic errors have been introduced in order to determine whether or not each datum is erroneous. The automated analysis that provides the greatest area under one or more ROCC curves generated from the analysis may be selected as the optimal clinical-laboratory-analysis method, given various other constraints, such as the amount and quality of data used to infer the clinical-laboratory analytical method.

Probability

Bayesian networks employ various concepts of probability and a dependency model to statistically model real-world situations and to facilitate statistical inference based on the statistically model. In this subsection, certain fundamental concepts related to probability discussed, to facilitate subsequence discussion of Bayesian networks.

Probability provides a framework for measuring the likelihood of the future occurrence of events, for inferring the likelihood of the past occurrence of events based on more recent observations, and for mathematically representing and modeling real-world situations that involve uncertainty and chance. In probability, a sample space S is a set of all possible outcomes for an experiment. For example, if the experiment is a toss of two-sided coins, each coin having a first side described as "head" or H, and a second side described as "tail" or T, then the sample space S for the experiment is: {HH, HT, TH, TT}. Each individual outcome, or groups of outcomes, are considered to be events. For example, the notation $E_{HH}$ may be used to represent the event that both tossed coins land heads up. As another example, the event $E_{one-head}$ may be the event that at least one of the two coins lands heads up, with:

$$E_{one-head} = \{E_{HH}, E_{HT}, E_{TH}\}$$

Set theory is frequently employed to represent various compound events, using the familiar set-theory operators "∪," "∩," and "\," which represent union, intersection, and set difference, respectively. For example:

$$S = \{E_{HH}\} \cup \{E_{HT}\} \cup \{E_{TH}\} \cup \{E_{TT}\}$$

A sample space may be finite, such as the outcomes of coin tosses, cards drawn from a deck of playing cards, and other discrete sample spaces, or may be countably infinite, such as a real-number measurement of a physical characteristic of a population of individuals. Probability may also be discussed with respect to random variables, essentially functions that map a probability space to a state space. A probability may be associated with each possible state of a random variable.

A probability can be associated with each event, or with each state of a random variable. If, for example, the random variable H is the measured height of a person, then a probability P(H=h) can be associated with each possible measured height h. The probability that a person will be measured to have a height of between 5'8" and 5'10", P(5'8"≦H≦5'10"), turns out to be the area on the probability distribution curve for measured heights (discussed in the previous subsection) between the standard deviation units corresponding to heights of 5'8" and 5'10". As another example, $P(E_{HH}) = ¼$.

There are 4 axioms that define probability:

1) $0 \leq P(E_i) \leq 1$

2) $P(S) = 1$

3) $P(E_1 \cup E_2) = P(E_1) + P(E_2)$

4) $P\left(\bigcup_{i=1}^{n} E_i\right) = \sum_{i=1}^{n} P(E_i)$, for $1 \leq n \leq N$ where $S \equiv \bigcup_{i=1}^{N} E_i$, and for all $1 \leq i \leq N$ and $1 \leq j \leq N$, with $i \neq j$, $E_i \cap E_j = \emptyset$ The first axiom states that probabilities associated with events, or states of random variables, range from 0 to 1. The second axiom states that some event within a sample space will occur, with certainty, as the outcome of an experiment. The third axiom states that the probability of a compound event is the sum of the probabilities of the component events of the compound event, given that the component events are mutually exclusive. The fourth axiom states that the probability of a compound event comprising the union of n events is equal to the sum of the probabilities of the n events, provided that the n events are mutually exclusive.

FIG. 6A shows a simple discrete probability distribution of a random variable T, in which T can take on one of six discrete values $t_1$, $t_2$, $t_3$, $t_4$, $t_5$, and $t_6$ with the probabilities indicated both numerically and by height of the histogram columns in FIG. 6A. The probability distribution shown in FIG. 6A is normalized. Because the probability distribution is normalized, the sum of the probabilities of the possible outcomes of a measurement is equal to one:

$$\sum_i P(t_i) = 1$$

Additional random variables based on the distribution of T can be defined. For example, a random variable $T_y$ can be defined as the occurrence of either $t_1$ or $t_4$, as follows:

$$T_y=\{t_1,t_4\}$$

The probability of the occurrence of the event, or measurement, represented by random variable $T_y$ is the sum of the probabilities in the occurrence of each of the individual, simple events $t_1$ and $t_4$:

$$P(T_y)=P(t_1)+P(t_4)=0.62+0.125=0.187$$

For the sake of illustration, consider three additional random variables $T_z$, $T_x$, and $T_w$:

$$T_z=\{t_3,t_4\}$$

$$T_x=\{t_4,t_6\}$$

$$T_w=\{t_2,t_4,t_6\}$$

The probability of occurrence of $T_y$ or $T_z$, upon a measurement, is computed as follows:

$$P(Ty \cup Tz)=P(Ty)+P(Tz)-P(Ty \cap Tz)=0.187+0.625-0.125=0.687$$

where $\cup$ indicates set union and $\cap$ represents set intersection.

Conditional probabilities frequently arise in the analysis and modeling of real-world situations. Using the above-defined compound events, the conditional probability that event $T_y$ has occurred, given that it is known that event $T_z$ has occurred, denoted $P(T_y|T_z)$, may be different than the probability that event $T_y$ has occurred, $P(T_y)$, if knowledge that the compound event $T_z$ has occurred changes the likelihood that $T_y$ has occurred. In this example, both $T_y$ and $T_z$ include the simple event $t_4$. Thus, upon having measured a system distributed according to T, knowledge that the measurement produced a value such that event $T_z$ has occurred makes it more likely that event $T_y$ has also occurred, since occurrence of $T_z$ eliminates the possibility that the measurement returned values $t_1$, $t_2$, $t_5$, or $t_6$. The conditional probability $P(T_y|T_z)$ is computed as:

$$P(T_y|T_z) = \frac{P(T_y \cap T_z)}{P(T_z)} = \frac{.125}{.625} = .2$$

Two compound events $T_y$ and $T_z$ are independent, Independent($T_y$,$T_z$), when $$P(T_y|T_z)=P(T_y)$$

Because $P(T_y|T_z)$ is not equal to $P(T_y)$ in the above example, the compound events $T_y$ and $T_z$ are not independent, denoted:

$$\neg \text{Independent}(T_y,T_z)$$

Two compound events may be dependent, such as $T_y$ and $T_z$ in the above example, but may be conditionally independent given additional information. Consider the following example based on probabilities associated with drawing a card from a standard deck of 52 playing cards. The event space $\Omega$ is defined as follows:

$$\Omega=\{A\clubsuit,A\diamondsuit,A\heartsuit,A\spadesuit,2\clubsuit,2\diamondsuit,\ldots,K\spadesuit\}$$

or is, another words, equal to the 52 playing cards. The compound event Jack, representing the drawing of a jack of any suit, is defined as:

$$\text{Jack}=\{J\clubsuit,J\diamondsuit,J\heartsuit,J\spadesuit\}$$

The compound event Royal, representing the drawing of a jack, queen, or king of any suit, is defined as:

$$\text{Royal}=\{J\clubsuit,J\diamondsuit,J\heartsuit,J\spadesuit,Q\clubsuit,Q\diamondsuit,Q\heartsuit,Q\spadesuit,K\clubsuit,K\diamondsuit,K\heartsuit,K\spadesuit\}$$

The compound event greater-than-7, or "GT7," representing the probability of drawing an 8, 9, 10, or royal card of any suit, is defined as:

$$\text{GT7}=\{8\clubsuit,8\diamondsuit,8\heartsuit,8\spadesuit,9\clubsuit,\ldots,K\spadesuit\}$$

It is easily determined that, upon drawing a card from a standard 52-card deck:

$$P(GT7) = \frac{6}{13}$$

$$P(\text{Royal}) = \frac{3}{13}$$

$$P(\text{Jack}) = \frac{1}{13}$$

The probability of drawing a card from the standard 52-card deck such that compound event GT7 occurs, but compound event Royal does not occur, is:

$$P(GT7 \cap \neg \text{Royal}) = \frac{3}{13}$$

where $\neg\text{Royal}=\Omega\backslash\text{Royal}=\{A\clubsuit,A\diamondsuit,\ldots,10\spadesuit\}$ This allows computation of the conditional probability of GT7 given $\neg$Royal is $$P(GT7 \mid \neg \text{Royal}) = \frac{\frac{2}{13}}{\frac{10}{13}} = \frac{3}{10}$$

By the definition of independence, provided above, it is readily seen that the compound events GT7 and ¬Royal are not independent.

Two events A and B are conditionally independent given a third compound event C when:

$$P(A \mid B \cap C) = P(A \mid C)$$

Defining the compound event Odd as follows:

Odd={A♣,A♦,A♥,A♠,3♣,3♦,3♥,3♠,5♣,5♦,5♥,5♠, ..., 9♠}

The conditional probability of compound event GT7 given occurrence of the compound event Odd is:

$$P(GT7 \mid \text{Odd}) = \frac{\frac{1}{13}}{\frac{5}{13}} = 0.2$$

and the conditional probability of GT7 given ¬Royal and Odd is:

$$P(GT7 \mid \neg \text{Royal}, \text{Odd}) = \frac{P(GT7 \cap \text{Royal} \cap \text{Odd})}{P(\neg \text{Royal} \cap \text{Odd})} = \frac{\frac{1}{13}}{\frac{5}{13}} = 0.2$$

Thus, according to the above-provided definition of a conditional independence, GT7 is independent from ¬Royal given occurrence of compound event Odd. This result is unsurprising, since the intersection of compound events Odd and ¬Royal is equal to compound event Odd. In words, the probability that a card drawn from a deck is greater than 7, given that as odd-numbered card was drawn, is independent of whether or not the drawn card is a royal card. In more interesting cases, conditional independence of events A and B, given C, may occur even when B∩C does not equal C.

Another important relationship involving conditional probabilities is Bayes' theorem, expressed as:

$$P(A \mid B) = \frac{P(B \mid A)P(A)}{P(B)}$$

Bayes' theorem can be best described using an example. Table 1, below, defines two events: (1) Analysis; and (2) Error Analysis:

TABLE 1

| Analysis | valid result |
| --- | --- |
|  | erroneous result |
| Error Analysis | error |
|  | no error |

The event Analysis refers to a clinical-laboratory analysis that can produce either a valid result or an erroneous result. The event "Error Analysis" refers to analysis of the clinical-laboratory result to determine whether or not the result represents an error. Consider the case when the following probabilities and conditional probabilities are known:

P(Analysis=error)=0.01

P(Error Anaylsis=error|Analysis=erroneous result) =0.8

P(ErrorAnalysis=error|Analysis valid result)=0.2

Thus, the probability that the clinical-laboratory analysis that provides an analytical result produces an erroneous result is one percent. The probability of error analysis detecting an erroneous result is 80 percent. The probability of error analysis incorrectly designating a valid clinical result as erroneous is 20 percent. Given the probability of a clinical-laboratory-analysis error and the conditional probabilities listed above, one might ask: "If, for a particular clinical-laboratory-analysis result, error analysis indicates that the result is erroneous, what is the probability that the clinical-laboratory-analytical result is actually erroneous?" More succinctly, one may wish to calculate or estimate:

P(Analysis=erroneous result|Error Analysis=error)

Bayes' theorem allows for computation of the desired probability as follows:

$$P(A = er \mid EA = e) = \frac{P(EA = e \mid A = er)P(A = er)}{P(EA = e \mid A = er)P(A = er) + P(EA = e \mid A = vr)P(A = vr)}$$

$$= \frac{0.8 \times .01}{(0.8)(.01) + (0.2)(.99)} = .039$$

In the above application of Baye's theorem, first-letter abbreviations are used for events and outcomes listed in Table 1. Thus, given the relatively low probability of a clinical-laboratory-analysis error, and the relatively poor sensitivity and specificity of error analysis, the probability that a clinical-laboratory-analytical result deemed to be erroneous by error analysis is actually erroneous is only approximately four percent.

Directed, Acyclic Graphs

Figure 6B:
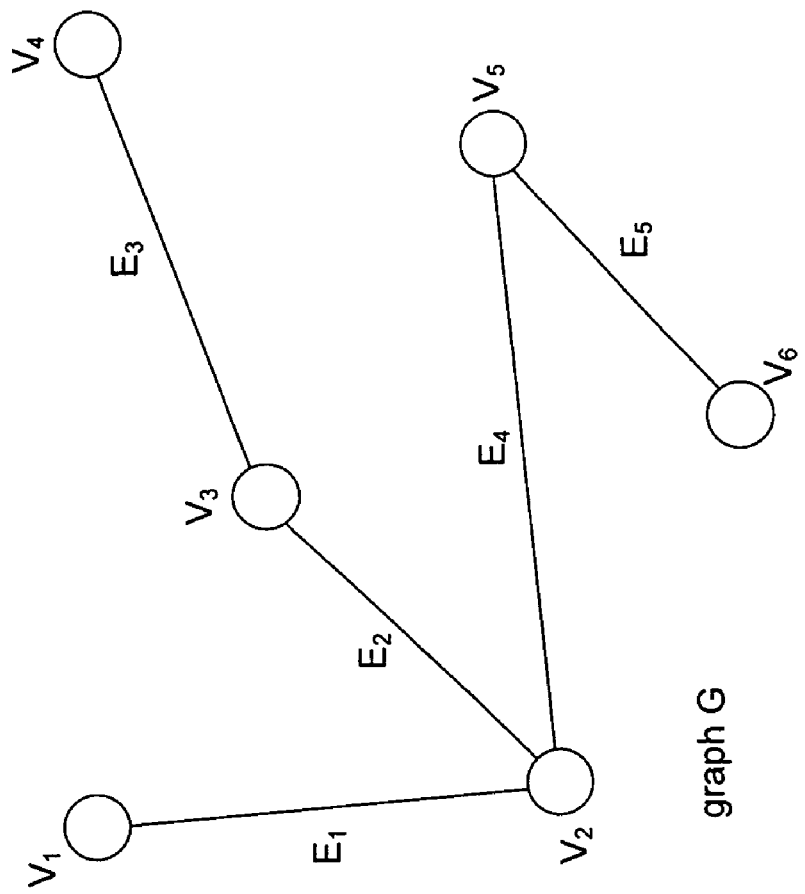
FIG. 6B shows a simple graph.

Graph theory is a branch of mathematics that has found wide applicability in computer science. Graphs are abstractions useful in modeling various types of relationships. A graph is a finite set of vertices, or nodes, and edges, each edge interconnecting a pair of vertices. FIG. 6B shows a simple graph. The graph 610 is represented as circles, each corresponding to a vertex, connected by lines corresponding to edges. For example, the graph 610 shown in FIG. 6B includes vertices $V_1$ and $V_2$ connected by edge $E_1$. The graph shown in FIG. 6B can be described, in set notation, as:

G={{$V_1,V_2,V_3,V_4,V_5,V_6$},{$E_1,E_2,E_3,E_4,E_5$}}

Figure 6C:
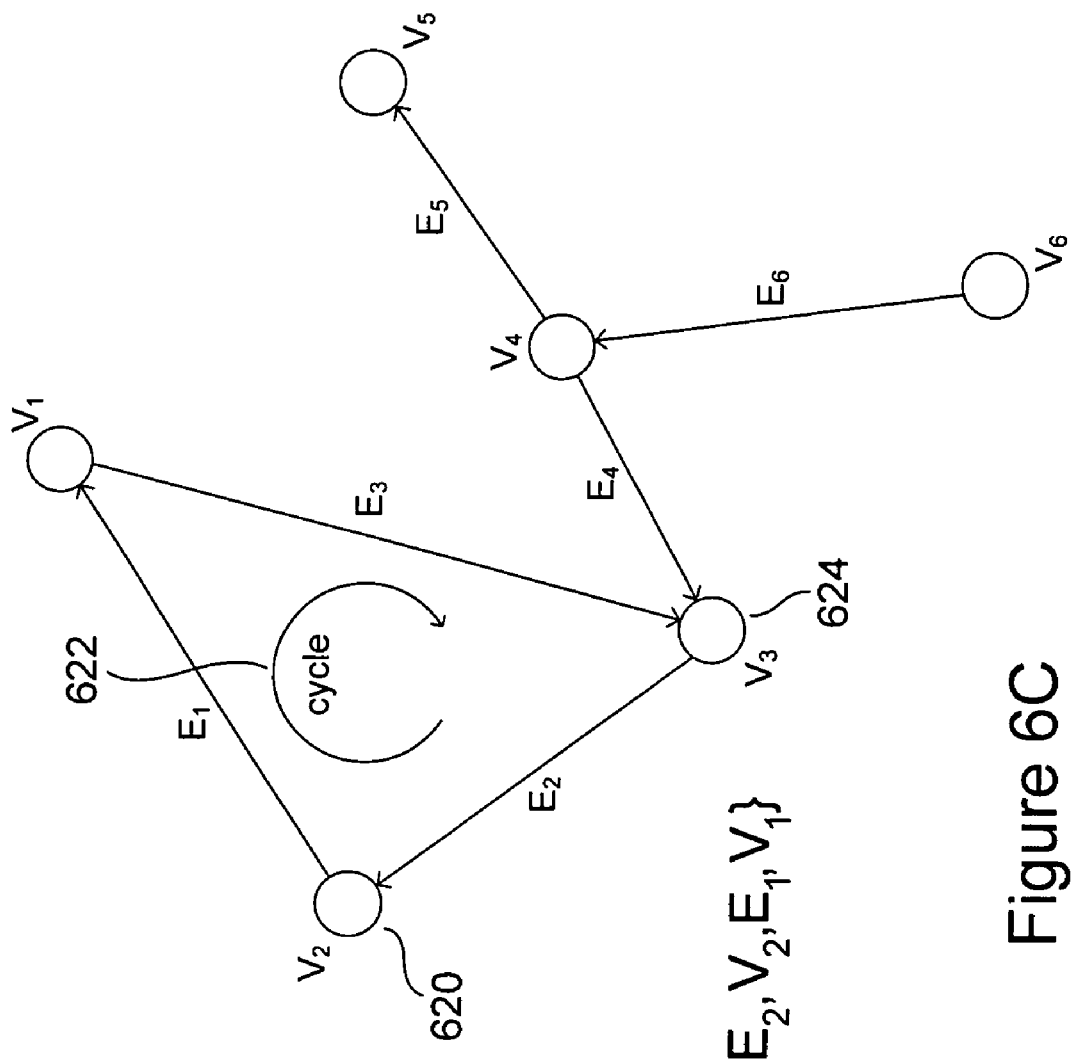
FIG. 6C shows a directed graph.
Figure 6D:
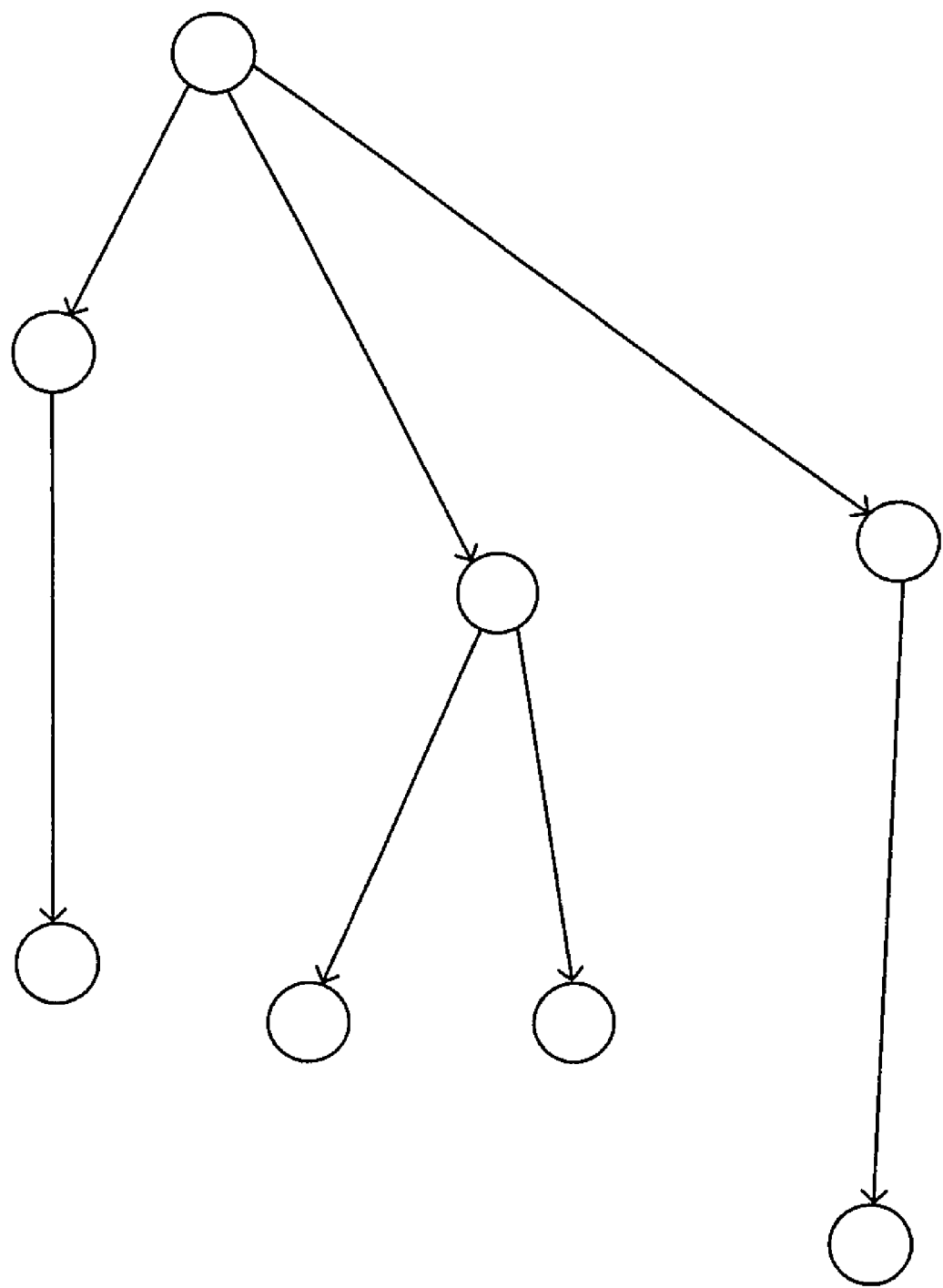
FIG. 6D shows a directed acyclic graph.

A directed graph is a graph in which edges are associated with directions. FIG. 6C shows a directed graph. The directed graph 620 includes 6 vertices and 6 edges. A directed path within a directed graph is a sequence of edges (and vertices connected by the edges) that interconnects a first vertex with a second vertex when the edges are traversed according to the directions associated with the edges. In graph 620 of FIG. 6C, vertex $V_6$ is connected to vertex $V_1$ by the path $\{V_6, E_6, V_4, E_4, V_3, E_2, V_2, E_1, V_1\}$. Vertices are commonly omitted from set descriptions of paths. When a vertex is connected to itself by a directed path, a cycle exists within a directed graph. For example, in the directed graph 620 shown in FIG. 6C, the path $\{E_2, E_1, E_3\}$ is a cycle 622 that connects vertex $V_3$ 624 with itself. A directed acyclic graph ("DAG") is a directed graph without cycles. FIG. 6D shows a DAG.

Bayesian Networks

Bayesian networks are abstract, computational structures that may be employed to statistically model real-world situations. A Bayesian networks can be considered to be an isomorphism between a DAG and a probability calculus. Bayesian networks allow for efficient statistical inference and abductive inference of various conditional probabilities from partially characterized joint probability distributions frequently encountered in real-world situations.

Another example of a statistical model, slightly more complicated than that discussed in the previous subsection, is used to illustrate the Bayesian-network approach to statistical inference. Table 2, provided below, defines five different random variables, each with two possible values: (1) S, indicating whether or not standard lab practices are followed in a particular clinical laboratory; (2) W, indicating whether or not a sample switch has occurred; (3) T, indicating whether or not a numerical transposition has occurred in a clinical-laboratory result; (4) E, indicating whether exhaustive error analysis has identified an error or not; and (5) C, indicating whether a consistency screen of clinical-laboratory results has indicated presence of an error or not.

TABLE 2

| | |
|---|---|
| S | s1 standard lab practices followed |
| | s2 standard lab practices not followed |
| W | w1 sample switch |
| | w2 no sample switch |
| T | t1 numerical transposition |
| | t2 no numerical transposition |
| E | e1 exhaustive error analysis → error |
| | e2 exhaustive error analysis → no error |
| C | c1 consistency screen → error |
| | c2 consistency screen → no error |

If the joint probability distributions for the five random variables are known, then the question "What is the probability that a sample switch has occurred, given that the clinical laboratory does not follow standard lab practices and given the fact that a consistency screen indicates the presence of an error?" can be computed as follows:

$$P(w1 \mid s2, c1) = \frac{\sum_t \sum_e P(w1, s2, c1, t, e)}{\sum_s \sum_c \sum_t \sum_e P(w1, s, c, t, e)}$$

In other words, one needs to sum the probabilities of all combinations of the random variables that include the values $w_1$, $s_2$, and $c_1$ and divide that sum by the sum of the probabilities of all combinations of random-variable values that include the value $w_1$. This computation presumes that the joint probability distributions for the random variables are known, which is often not the case. Moreover, for any reasonably large model, with many tens of random variables, each of which may have from two to tens of different possible values, the computation is often completely infeasible, due to the combinatoric explosion involved with computing sums of exponentially large numbers of individual probabilities.

Figure 7:
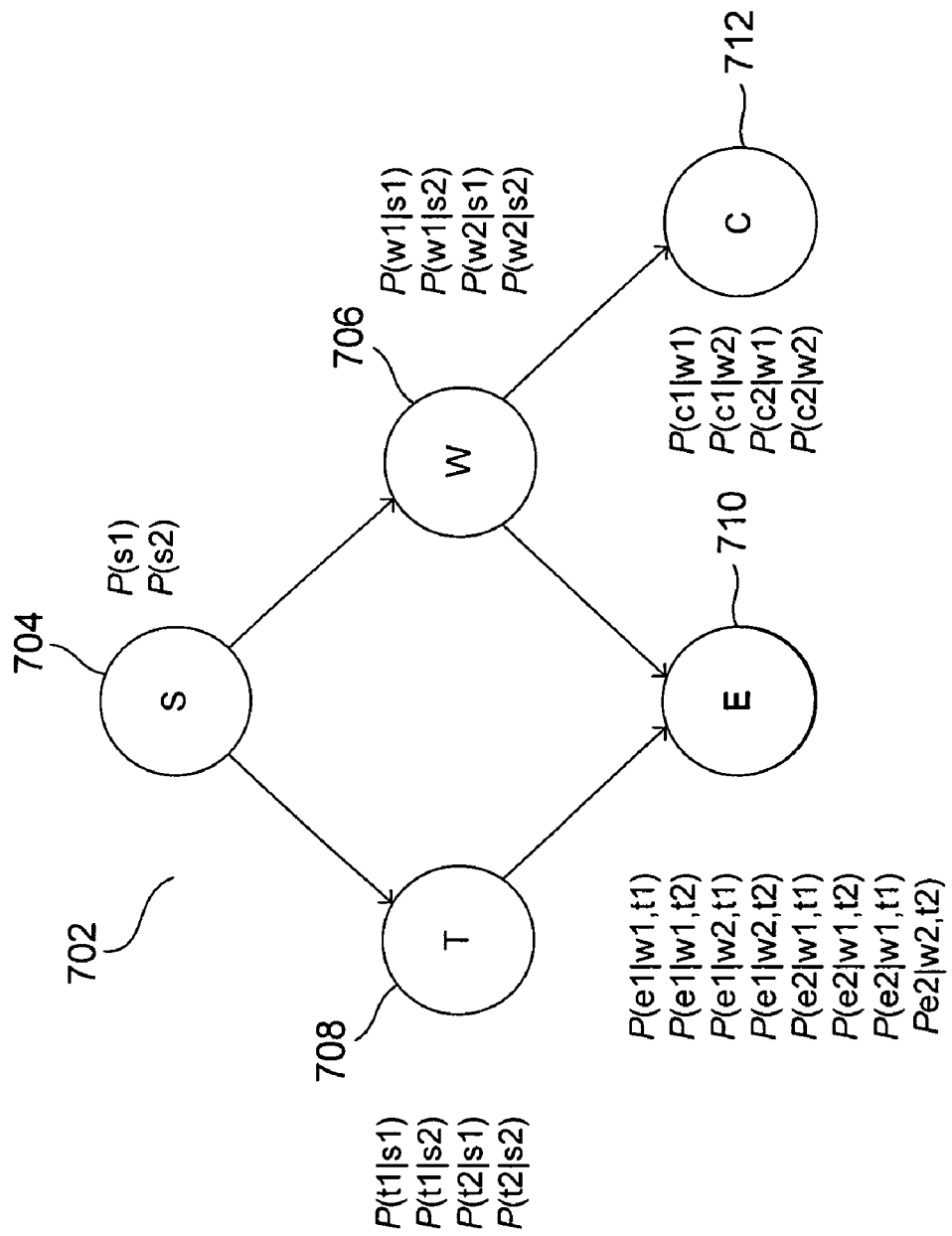
FIG. 7 shows an exemplary Bayesian-network model.

Bayesian networks have been designed to address the problems of incomplete knowledge of joint probability distributions and computational infeasibility of statistical inference based on joint probability distributions. FIG. 7 shows an exemplary Bayesian-network model for the example introduced in Table 2, above. The Bayesian network 702 is a directed acyclic graph ("DAG") with nodes representing random variables and with directed edges linking pairs of nodes related by causation. In the Bayesian network shown in FIG. 7, for example, node 704 represents the random variable S indicating whether or not standard laboratory practices are followed in a particular clinical laboratory. Whether or not standard laboratory practices are followed is considered to determine, at least in part, the probability of the occurrence of a sample switch 706 or a numerical transposition 708 in clinical-laboratory-analysis results generated by the clinical laboratory. The occurrence of a numerical transposition or sample switch, in turn, together determines whether or not exhaustive error analysis 701 of a result produced by the clinical-laboratory is erroneous. The occurrence of a sample switch error 706 also determines whether or not a consistency screen 712 detects an error in a result produced by the clinical laboratory.

Bayesian networks include probabilities for root-node values and conditional probabilities for internal nodes and leaf nodes, given values for parent nodes, as shown in FIG. 7. A Bayesian network is constructed so that, for any node X, the node X is conditionally independent of any non-descendent nodes of X within the Bayesian network given the conditional probabilities associated with the parent nodes of node X, expressed as:

$$I(X, ND_X \text{ given } PA_X)$$

where $ND_X$ denotes all nodes that are not descendants of X, and $PA_X$ denotes the parent nodes of X.

Bayesian networks are also constructed so that only the functional dependencies entailed by causation represented by directed edges in the Bayesian network are entailed by the model. This, in turn, allows for efficient computational inference. If one can determine particular values for the random variables represented by a set of j nodes, J, in the Bayesian network or, more succinctly:

$$J = \{j \text{ instantiated nodes } J_1, J_2, \ldots, J_j\}$$

and if the remaining k nodes K are uninstantiated or, more succinctly:

$$K = \{k \text{ instantiated nodes } K_1, K_2, \ldots, K_k\}$$

then one can determine the conditional probabilities of all of the uninstantiated nodes given the instantiated nodes, $P(K_i|J)$, for i=1 to k. In the example shown in FIG. 7, if it is known that the consistency screen returned an error, or C is instantiated to be c1, then conditional probability of a sample switch based on the occurrence of c1 can be computed as follows:

$$P(w1 \mid c1) = \frac{P(c1 \mid w1) P(w1)}{P(c1)}$$

Furthermore, the conditional probability that standard laboratory practices were followed, given that the consistency screen returned an error, can be computed, using Bayes' theorem, as follows:

$$P(s1 \mid c1) = \frac{P(c1 \mid s1) P(s1)}{P(c1)}$$

Thus, Bayes' theorem can be used to compute conditional probabilities for nodes above instantiated nodes. Similarly, if it is known that standard laboratory practices are followed, or s1, then the conditional probability that a sample switch has occurred, given s1 is immediately known, and the conditional probability that a consistency screen will return an error given that standard laboratory practices have been followed can be computed as:

$$P(c1 \mid s1) = P(c1 \mid w2, s1) P(w2 \mid s1) + P(c1 \mid w1, s1) P(w1, s1)$$

Thus, conditional probabilities can be inferred in a downward direction. A variety of different efficient computational algorithms for computing conditional probabilities based on instantiated nodes have been devised, including various message-passing algorithms for passing information in both directions between linked nodes.

Finally, Bayesian networks allow for abductive inference. Abductive inference involves determining the most likely cause of a particular observed event. Efficient computational algorithms have been developed to compute the most probable explanation ("MPE") as the most likely values of uninstantiated nodes that would explain the values of instantiated nodes, as follows:

$$MPE = \frac{\arg \max}{K_1, K_2, \ldots, K_k} P(J_1, J_2, \ldots, J_j \mid k_1, k_2, \ldots, k_K)$$

Thus, abductive inference allows one to determine the most probable hypothesis for the occurrence of one or more events.

EMBODIMENTS OF THE PRESENT INVENTION

Various embodiments of the present invention employ ROCCs and Bayesian networks or modified Bayesian networks for analysis of clinical-laboratory results in order to detect errors. Use of Bayesian networks and modified Bayesian networks provide numerous advantages. First, when a proper Bayesian network is inferred from clinical-laboratory-result training sets, computationally efficient statistical inference can be carried out to detect a wide variety of different types of errors based on known causation relationships between different random variables used to model clinical-laboratory results. The conditional probabilities that define nodes within a Bayesian network are readily accessible and readily understood, unlike complex logic rules used in expert systems. Bayesian networks are relatively easily modified, updated, and optimized, unlike rule-based systems. Moreover, Bayesian networks, as discussed in the preceding subsection, can be used for abductive inference as well as for inferring various conditional probabilities. Thus, not only can clinical-laboratory errors be detected in clinical-laboratory-result data sets, but the most probable explanations for the errors can be determined as feedback to clinical laboratories in order to modify and optimize clinical procedures to prevent those errors in the future. Automated error-detection systems are potentially far more cost effective and more accurate than manual error detection that relies on panels of human experts. As automated error-detection systems grow increasingly competent through refinement and feedback, they can be immediately applied in a large number of of clinical laboratories to many different data sets, while well-trained human experts can offer only a limited error-detection bandwidth.

Figure 8A:
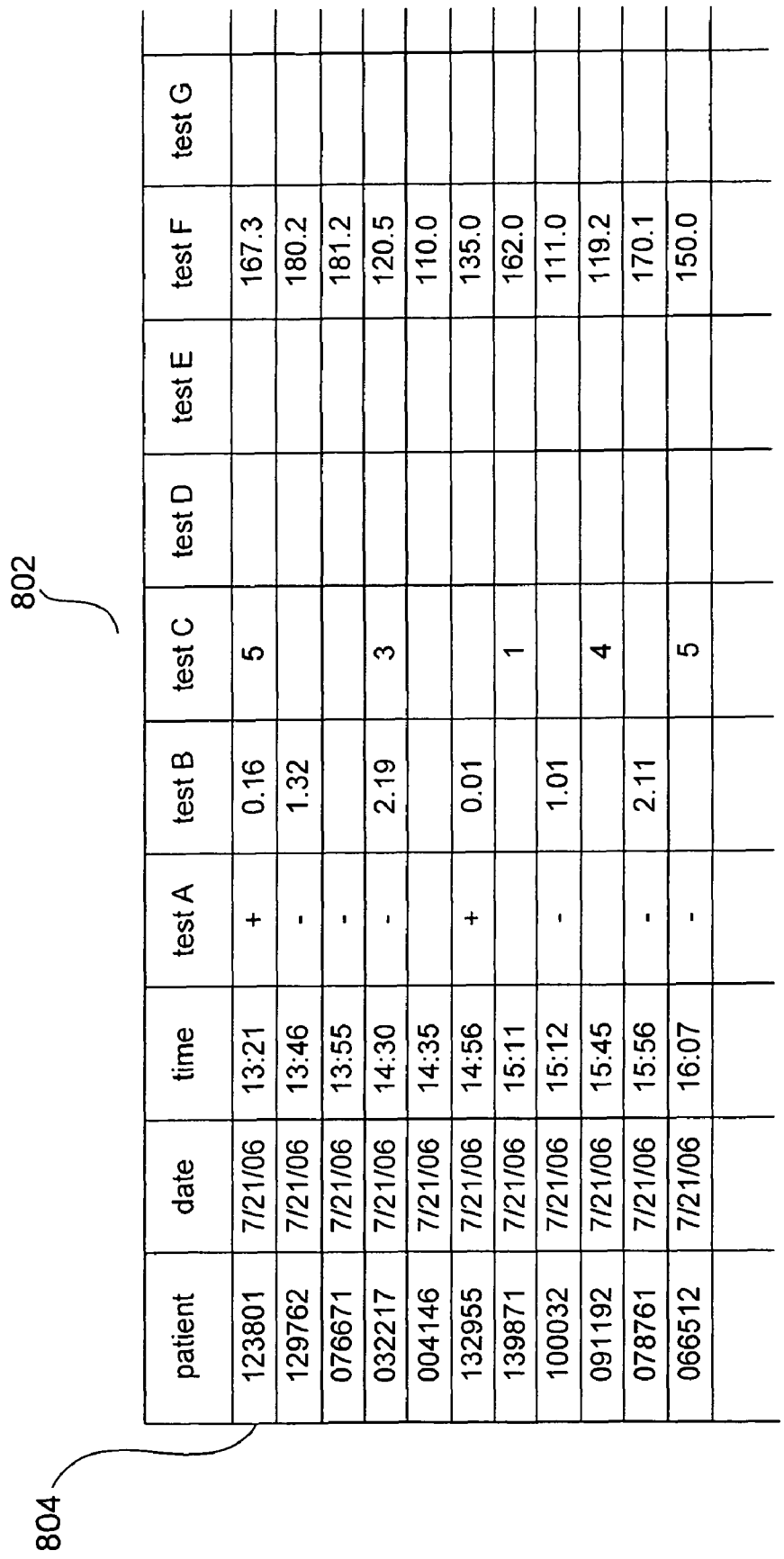

FIGS. 8A-F illustrate a portion of an exemplary clinical-laboratory-analysis-results data set and various types of errors that may arise in clinical-laboratory-analysis-result data sets. FIG. 8A shows a portion of tabulated clinical-laboratory-analysis results produced over a few hours. Each line of the results table, such as line 804, describes the results of one or more tests produced for a particular patient on a particular date and at a particular time. For example, line 804 of results table 802 in FIG. A indicates that the patient identified by the patient ID 123801 was subjected to tests A, B, C, and F, results of which were produced at 1:21 PM on Jul. 21, 2006. Of course, an almost limitless number of different results-data-set formats and encodings are possible, and, in other embodiments, each test may be separately tabulated and cross-indexed with patient tables and additional information. For example, the date and time at which each sample for a particular test was taken from a patient and the time that the sample was processed may also be included. There may be many different types of test results. For example, the results of test A in the results table shown in FIG. 8A are reported as either "+" or "−," depending on whether test A indicates a positive or negative result. In other words, test A produces binary results. By contrast, tests B and F produce rational-number results, with the test results reported up to a particular accuracy or number of decimal places. Test C produces small-integer results in the range 1-5. Many other types of results are possible.

FIG. 8B illustrates one type of clinical-laboratory-analysis error referred to as a "value error." FIG. 8B shows the first few lines of the result table 802 shown in FIG. 8A that include a single value error 806 circled for clarity. The value error comprises a transposition of the digits "6" and "1" to produce an erroneous test result. The result of test B reported for patient 123801 is 0.61, rather than the correct result of 0.16. FIG. 8C illustrates a sample-processing error. As shown in FIG. 8C, the results for tests A and B 808 for patient 123801, shown circled in FIG. 8C, are markedly different than the correct results shown in FIG. 8A. The result of test A is negative, rather than positive, and the result of test B is 1.66, rather than the correct result 0.16. This sampling error may have arisen because of instrumental errors, faulty procedures in collecting and handling a sample taken from the patient, and other such errors. FIG. 8D illustrates a sample-switch error. In FIG. 8D, the results of test of A and B 810 for patient 123801 and patient 129762 have been interchanged. Sample-switch errors can occur due to patient misidentification, sample interchanges, labeling errors, and other such errors. In general, value errors each affect a single, discrete result. Sample-processing errors generally affect a known set of two or more analytical results for a collected sample, and do so in generally predictable manners. Sample-switching errors affect multiple test results for multiple patients. In a gross sample-switching error, referred to as "patient misidentification," all samples for a particular patient may be switched with those for another patient. Value errors, sample-processing errors, and sample-switch errors are representative of the types of errors that may occur in clinical-laboratory-analysis results. Various embodiments of the present invention are directed to discovering these types of errors in large clinical-laboratory-analysis-result data sets.

The statistical model incorporated in a Bayesian-network embodiment of the present invention that is used to detect various types of clinical-laboratory-analysis-result data-set errors may rely on a number of different relationships between various data-set values. For example, FIG. 8E illustrates an error detectable from a history of test results for a particular patient. In FIG. 8E, test results for test A and B are shown for the same patient produced on seven successive days. In all but one case, test A produces a negative result, and test B produces a rational-number result within a relatively narrow range of 1.63-1.87. However, on Jul. 5, 2006, the results for patient 123804 for test A and test B are positive and 0.10, respectively. This potentially erroneous test result, circled 812 in FIG. 8E, is inconsistent with regularly produced test results for the same patient.

Figure 8F:
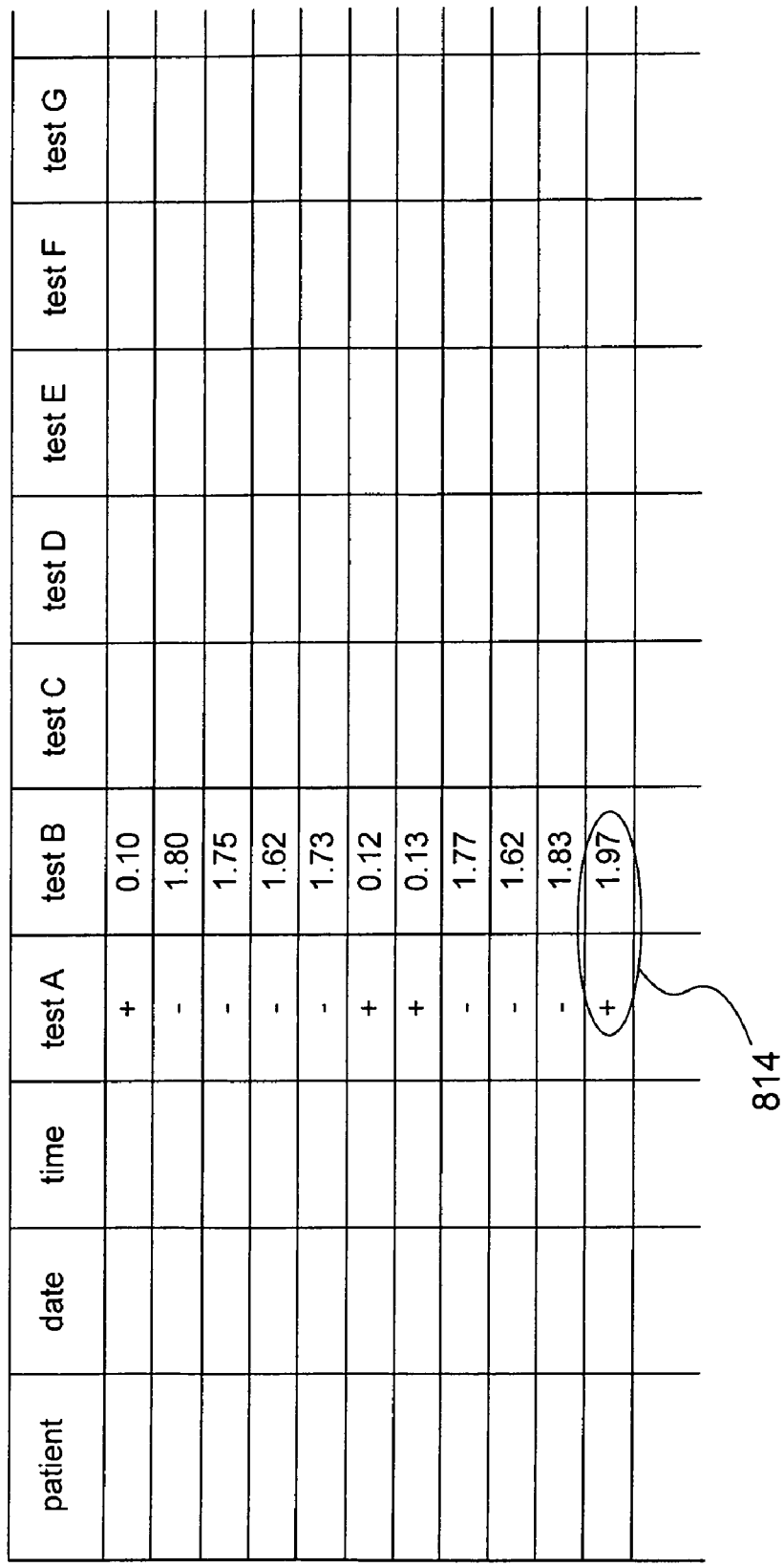

FIG. 8F illustrates a second type of data dependency that may be used to identify errors. FIG. 8F shows a variety of test results for tests A and B. As can be seen by observing the column of test results for test A and B, test B appears to produce relatively low values, in the range of 0.1-0.13, when test A shows a positive result. When test A shows a negative result, test B generally has relatively high-valued results, in the range 1.62-1.83. However, the circled result 814 departs from this pattern. In the circled result, test A shows a positive result, while test B produces a very high-valued result of 1.97. The combination of a very high result for test B and a positive result for test A markedly departs from the normally observed pattern, and may be indicative of an erroneous result reported for test A and B. Moreover, even when the test B portion of the erroneous result 814 alone is compared to the remaining test B results, the erroneous result for test B result has a substantially higher value than any of the other test B results, and may therefore be further indicative of an error in the results for test A and B 814 circled in FIG. 8F.

The two types of dependency relationships illustrated in FIGS. 8E and F represent only a small portion of the many different possible functional relationships and causation relationships between data within a clinical-laboratory-analysis-result data set. Many of these types of dependencies and causation relationships can be modeled in a Bayesian network designed to detect clinical-laboratory-result errors according to method embodiments of the present invention. In certain embodiments of the present invention, the dependencies and causation relationships are inferred by employing a training data set to construct a Bayesian network. In other embodiments, the dependencies and causation relationships can be identified by human experts and encoded into the Bayesian network, which can be further optimized and augmented using training-set data.

Figure 9:
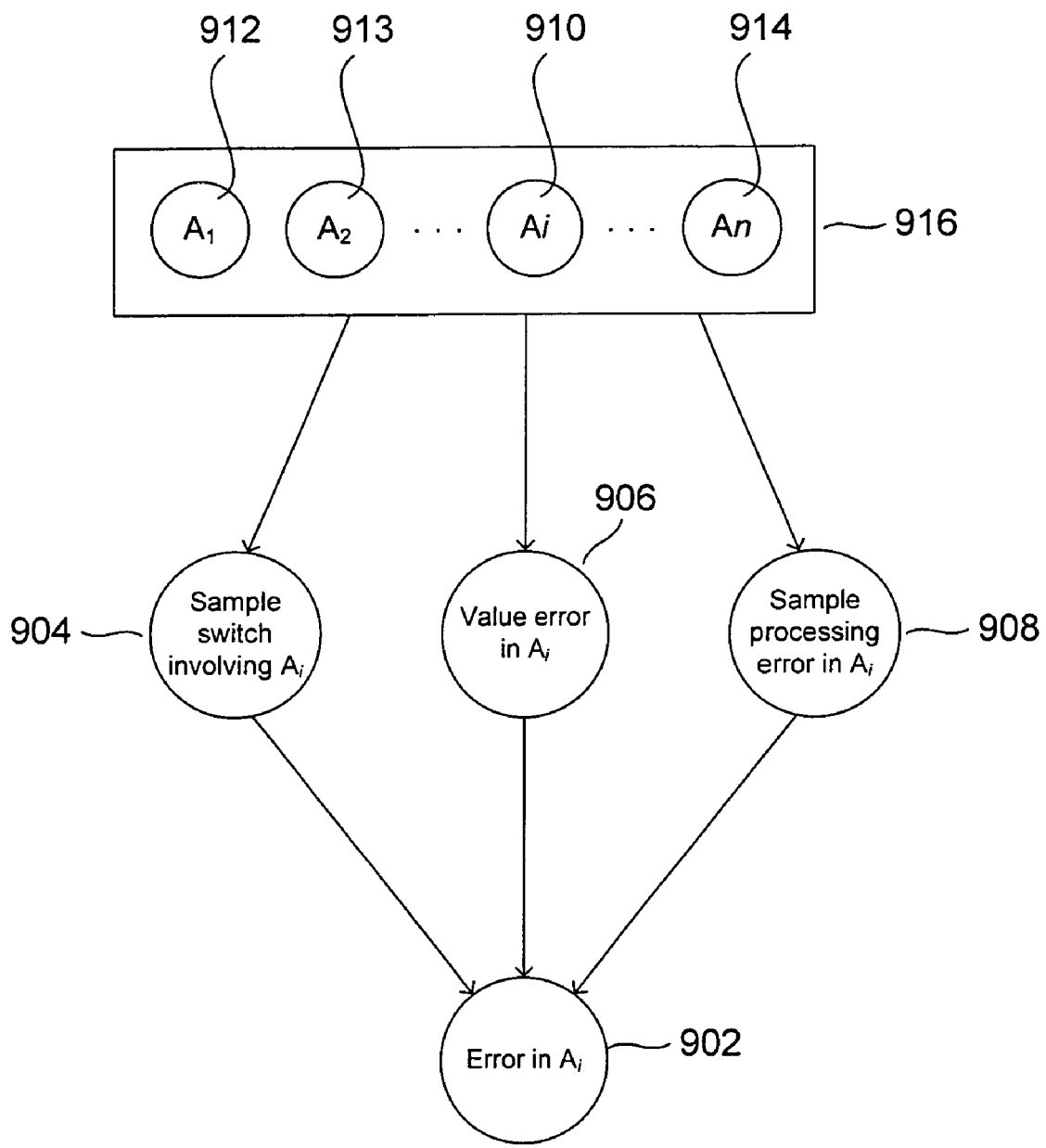
FIG. 9 illustrates a portion of a modified Bayesian network in which functionally dependent nodes are gathered together into a collective node in order to avoid explicitly identifying causation among the functionally dependent nodes and between the functionally dependent nodes and other nodes in the Bayesian network.

In various embodiments of the present invention, the DAG-based Bayesian network, an example of which is shown in FIG. 7, may be modified in order to overcome a lack of information concerning the causation relationships between random variables represented by nodes in the Bayesian network. FIG. 9 illustrates a portion of a modified Bayesian network in which functionally dependent nodes are gathered together into a collective node in order to avoid explicitly identifying causation relationships among the functionally dependent nodes and between the functionally dependent nodes and other nodes in the Bayesian network. In FIG. 9, node 902 represents the occurrence of an error in an analytical result $A_i$. The error may occur due to a sample switch involving result $A_j$ 904, a value error in results $A_i$ 906, or a sample processing error in $A_i$ 908. The probabilities of the sample switch 904, value error 906, and sample processing error 908 may, in turn, be functionally dependent on interrelationships between result $A_i$ 910 and other analytical results 912-914. However, these dependencies may be dynamic, poorly defined, or themselves dependent on additional criteria that are not well understood or captured in the model. For example, instantiation of node 908 to indicate that a sample processing error has not occurred for analytical result $A_i$ may alter the confidence in analytical results $A_1, A_2, \ldots A_n$ as well as alter the dependencies between the analytical results and the collective node 916. Therefore, by using a Bayesian network modified to include collective nodes of functionally-dependent variables, the resulting modified Bayesian network may be substantially simpler and more reflective of the current understanding of dependencies within clinical-laboratory-analysis-result data sets.

Figure 10:
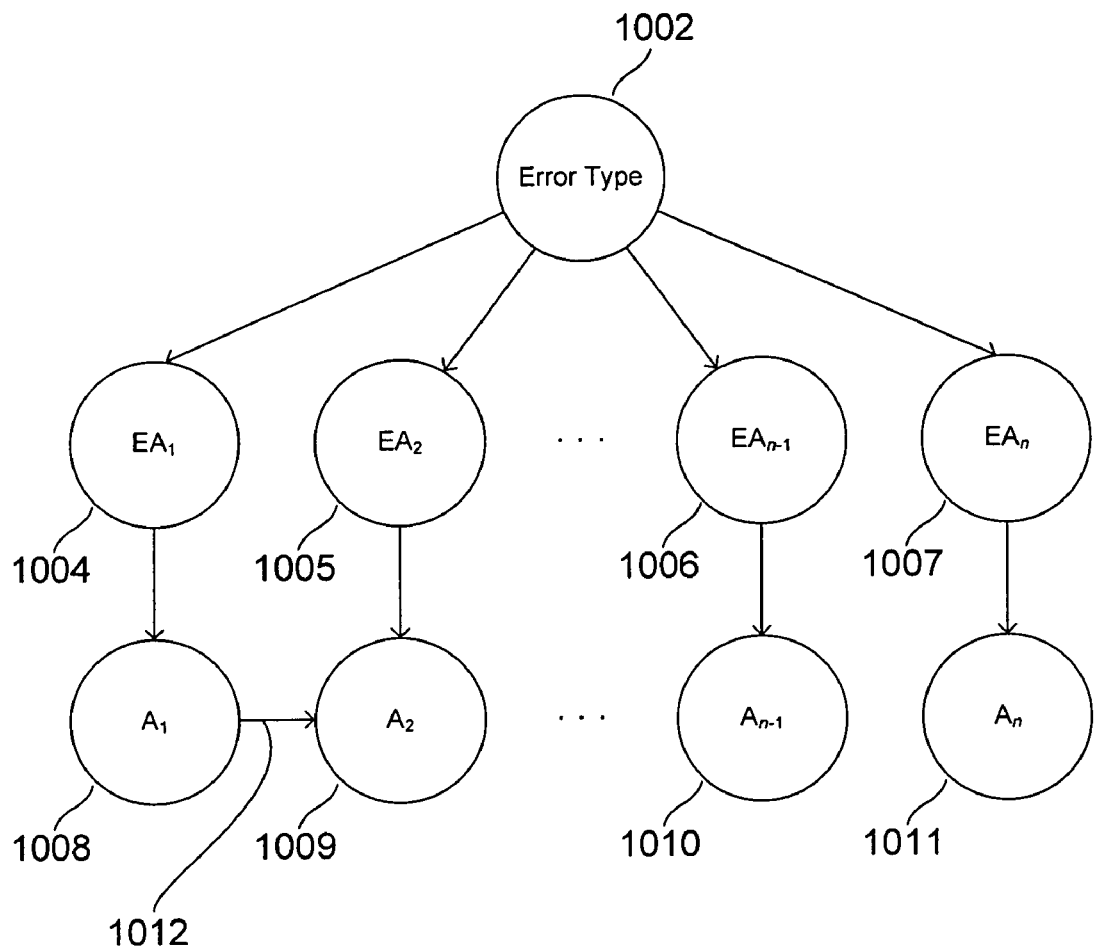
FIG. 10 illustrates a second type of modified Bayesian network.

FIG. 10 illustrates a second type of modified Bayesian network. FIG. 10 shows a small portion of a modified Bayesian network, referred to as an "analyte-child network." In this network, an error-type node 1002 has directed edges to each of a number of analyte-specific error nodes 1004-1007, each, in turn, having a directed edge to a particular, corresponding analyte node 1008-1011. Analytical results that statistically co-vary have directed edges between them, such as directed edge 1012 in FIG. 10. Statistical covariance between analytical results can be determined by techniques used to optimize a Bayesian network for analysis of training sets. Again, like functional-dependency networks, described above with reference to FIG. 9, the analyte-child network described with reference to FIG. 10 may lead to simpler modified Bayesian networks that can be optimized to detect covariance of various analytical results. Many other Bayesian-network modifications may be used to simplify and better capture knowledge about dependencies between clinical-laboratory-analysis-result-data-set values and to reflect those dependencies discovered during Bayesian-network construction and optimization.

Figure 11:
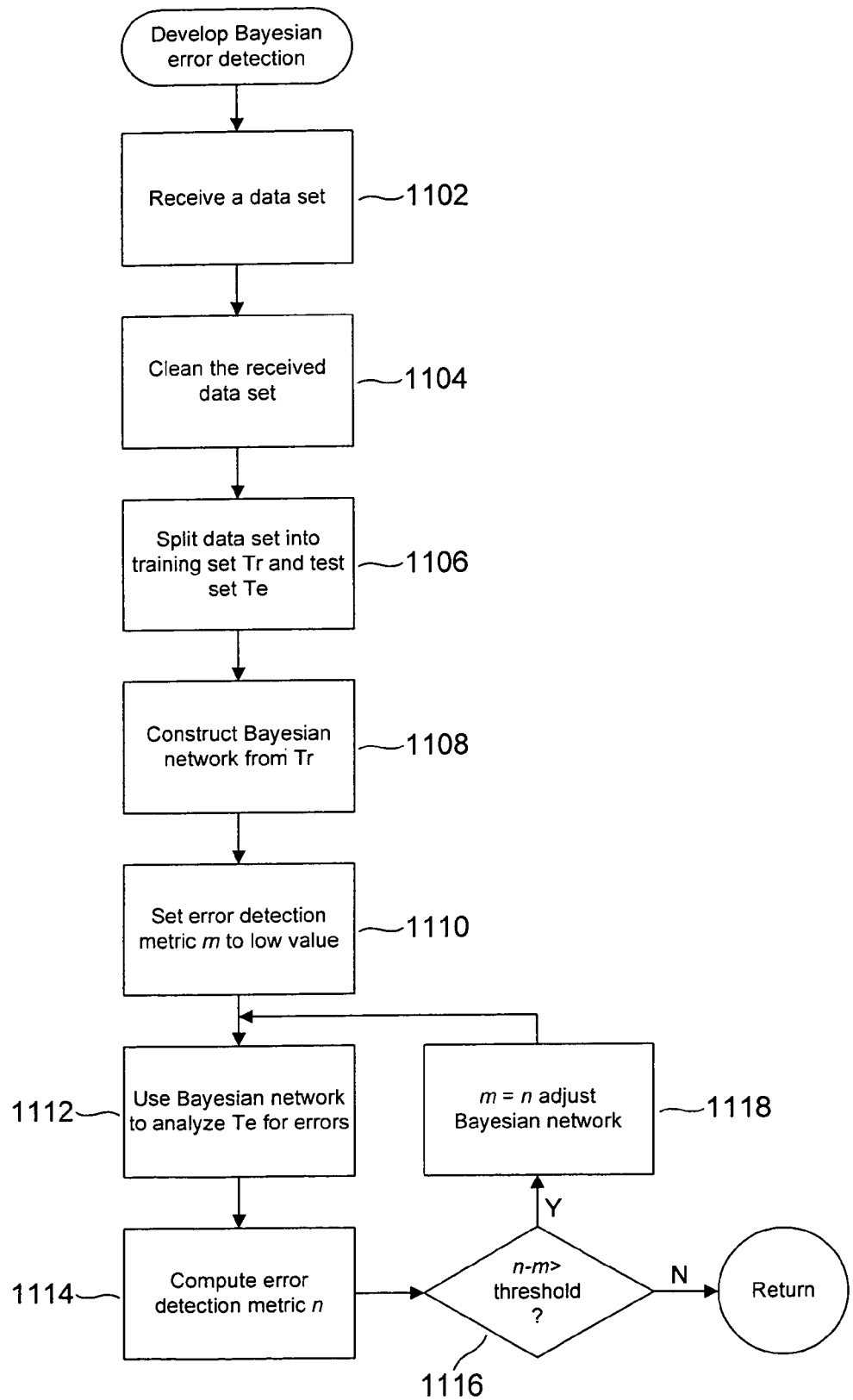
FIG. 11 is a control-flow diagram that describes one embodiment of the present invention.

FIG. 11 is a control-flow diagram that describes one embodiment of the present invention. In this embodiment, a Bayesian network or modified Bayesian network for detecting errors in clinical-laboratory-analysis-result data sets is constructed and optimized. In step 1102, a clinical-laboratory-analysis-result data set is received. In step 1104, the received data set is cleaned by manual analysis. A panel of human experts is used to detect and remove or correct erroneous results to produce a cleaned data set. In step 1106, the cleaned data set is split into a training set Tr and a test set Te. In certain embodiments, the clean-data-set splitting operation produced equally sized training data set Tr and test data set Te, while, in other embodiments, the split is uneven in order to produce a training data set and test data set optimally sized for Bayesian-network construction and Bayesian-network verification, respectively. In certain embodiments of the present invention, the data split is carried out on a random or pseudorandom basis. Synthetic errors that represent the various types of error, including value errors, sample-processing errors, and sample-switch errors, are devised and inserted into the training and test data sets. These synthetic errors are well known, and can be later used to determine the accuracy of error detection by the Bayesian-network or modified-Bayesian-network error-detection system constructed using the training data set and test data set.

Next, in step 1108, a Bayesian network is inferred or partially inferred from the training set. For example, a rudimentary Bayesian network may be developed based on known data dependencies and causation relationships and other criteria, and the rudimentary Bayesian network may be modified and supplemented by adjusting conditional probabilities contained within the Bayesian-network nodes to match conditional probabilities inferred from the training data set, as well as to add additional nodes and edges to reflect additional data dependencies discovered during the construction process. Next, in step 1110, an error-detection metric m is set to a low value. This metric may be, for example, reflective of the area under an ROCC curve, or the combined areas under multiple ROCC curves used to analyze the sensitivity and specificity of the constructed Bayesian network. In step 1112, the Bayesian network is used to analyze the test set Te for errors. In step 1114, a detection metric n can be computed for the Bayesian-network error analysis carried out in step 112, since all errors in the test data set Te were synthetically generated and inserted into the clean data set used in step 1104. When the current Bayesian network has shown an improvement in sensitivity and specificity with respect to the previous Bayesian network, as determined in step 1116, then m is assigned to n and the Bayesian network is adjusted, in step 1118, or modified, in order to better reflect the dependencies and conditional probabilities gleaned from analyzing the Bayesian network's ability to detect errors, in step 1114. The adjusted and updated Bayesian network is then used, in step 112, to again analyze the test set Te. When the Bayesian network has been adjusted and modified so that improvements between the adjusted and modified Bayesian network and the previous Bayesian network are less than a threshold value, as determined in step 1116, then the current Bayesian network is accepted as optimal or near-optimal.

Although the present invention has been described in terms of particular embodiments, it is not intended that the invention be limited to these embodiments. Modifications within the spirit of the invention will be apparent to those skilled in the art. For example, any number of different sources of clinical-laboratory-analysis-result data sets may be collected and combined in order to produce training data sets and test data sets. The Bayesian networks or modified Bayesian networks constructed by, and used in, various embodiments of the present invention may be programmed and encoded in an almost limitless number of different ways by varying control structures, variables, organization of, and other parameters of control code and varying the encodings of conditional probabilities, nodes, and edges used to store a Bayesian network in computer memory and on mass storage devices. In various embodiments of the present invention, only discrete-valued random variables, or both discrete-valued random variables and continuous-valued random variables may be included in the Bayesian network to accurately model various types of clinical-laboratory-analysis-result data sets and functional dependencies between data values. The Bayesian networks may be constructed based on dependencies known to human experts, based on dependencies inferred from training data sets, based on a based on a combination of inferred dependencies, by a variety of other means.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A method for detecting errors in a clinical-laboratory-analysis-results data set, the method comprising:
   receiving a cleaned clinical-laboratory-analysis-results data set;
   introducing synthetic errors into the cleaned clinical-laboratory-analysis-results data set to produce a training data set and a test data set;
   inferring a Bayesian network or modified Bayesian network, based on the training data set, for detecting errors;
   evaluating and optimizing the Bayesian network or modified Bayesian network, using the test data set to produce a final Bayesian network or modified Bayesian network; and
   using the final Bayesian network or modified Bayesian network to detect errors in subsequently received clinical-laboratory-analysis-results data sets.

* * * * *